United States Patent [19]

Drewlow

[11] Patent Number: Plant 6,395

[45] Date of Patent: Nov. 15, 1988

[54] STREPTOCARPUS PLANT NAMED MUSE

[75] Inventor: Lyndon W. Drewlow, Ashtabula, Ohio

[73] Assignee: Mikkelsens, Inc., Ashtabula, Ohio

[21] Appl. No.: 9,375

[22] Filed: Jan. 30, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Streptocarpus plant named Muse characterized by its rosette plant form, red-purple flower color with darker streaking, compact growth habit, floriferous habit, ease of propagation, tolerance to light and temperature, small, pliable leaves, and by its long lasting and non-shattering flowers.

1 Drawing Sheet

The present invention relates to a new and distinct cultivar of Streptocarpus plant, botanically known as *Streptocarpus×hybridus,* and known by the cultivar name Muse. Muse was developed by me through controlled breeding by crossing Mikkelsen Seedling 82-1096-8 (seed parent)×Mikkelsen Seedling 82-1175-8 (pollen parent).

Asexual reproduction by leaf cuttings has shown that the unique features of this new Streptocarpus are stabilized and are reproduced true to type in successive propagations.

The following characteristics distinguish the new Streptocarpus from both its parent varieties and other cultivated Streptocarpus of this type known and used in the floriculture industry:

1. Muse is a darker lavender pink than Diana but lighter than Adonis. It is similar in color to Juno but does not have as much yellow in the throat. Diana, Adonis and Juno are unpatented cultivars.

2. Muse has more flower stalks in bloom at one time than Diana, Adonis and Juno, but not as many as Janus and Orion, with both Janus and Orion being disclosed in pending plant patent applications. Muse has an average of 4 blooms per bloom stalk.

3. Muse has numerous short leaves in a rosette instead of one large leaf that characterizes many Streptocarpus cultivars. This results in a cluster of flowers in the middle of green foliage making an attractive 10 cm flowering plant.

4. Muse has smaller, more pliable leaves than Diana, Juno, and Adonis, and thus is very good for shipping. The leaves are similar to Orion, Janus, and Pegasus, with the latter also being disclosed in a pending plant patent application.

5. From a well rooted plant out of a 72 cell pack, Muse develops into a flowering plant in 6 to 8 weeks, which is approximately 7 days earlier than Diana, Juno and Adonis.

6. Plant habit and size is similar to Janus and Orion but not as compact as Minerva and Pegasus. It is more compact than Achilles, Juno, Adonis and Diana. Minerva and Achilles are also disclosed in pending plant patent applications.

7. Muse has shown the ability to flower both under the low light conditions of winter (December to February) and under the higher temperatures of summer (July to September) without ever going out of bloom under greenhouse conditions.

8. It has also shown the ability to tolerate watering with colder than normal water (40° F.) without foliar spotting and to tolerate fairly high light levels in summer without leaf yellowing or bronzing which is not the case with Apollo, an unpatented cultivar.

9. Numerous plantlets of Muse are formed from leaf cuttings in 8 to 10 weeks depending on the time of year. Muse is similar to Electra and Ariadne in leaf propagation, but not as good as Janus and Orion. Both Electra and Ariadne are disclosed in pending plant patent applications.

10. Muse has flowers similar in size to Janus, but not as large as Achilles, Juno, Adonis and Diana. However, Muse has more flowers at one time thus producing a colorful display.

The accompanying color photograph illustrates in perspective view the overall appearance of the cultivar, with colors being as true as it is reasonably possible to obtain in a color reproduction of this type.

The following is a detailed description of my new Streptocarpus cultivar based on plants produced under commercial practices in the greenhouses of Mikkelsens Inc., Ashtabula, Ohio. Color references are made to The Royal Horticultural Society Colour Chart (RHS), except where general colors of ordinary dictionary significance are used.

Classification:

*Botanical.—Streptocarpus×hybridus,* cv. Muse.

Parentage: Controlled cross between Mikkelsen seedling 82-1096-8 and Mikkelsen seedling 82-1175-8.

Propagation:

A. *Type cutting.*—Leaf.

B. *Time to develop plantlets.*—Summer: 8 weeks at 20° C.; Winter: 10 weeks at 20° C.

C. *Rooting habit.*—Numerous, fine, fibrous.

Plant description:

A. *Form.*—Leaves are rosette from a crown at the soil line, with flower stalks forming at the leaf midrib. Many leaves in a symmetrical pattern.

B. *Habit of growth.*—Vigorous, very free flowering, never going out of bloom once it starts blooming under greenhouse conditions. Flowers carried above foliage.

C. *Height from soil line.*—20 to 22 cm at maturity to top of bloom.

D. *Spread.*—40 to 50 cm at maturity. Leaf Size: 20 to 22 cm in length and 7 to 8 cm in width at the widest point; leaf size can vary greatly with cultural conditions. Quantity: Mature plant can have more than 20 leaves. Leaf Shape: Elliptical. Texture: Lower surface rugose with veins protruding and pubescent — upper surface rugose and pubescent. Margin: Finely crenate. Color: Young foliage top side 137A; under side 138C. Mature foliage top side 139A; under side 146C. Ribs and veins: Pinnate. Rib and vein color: 137C. Leaf tips: Obtuse. Leaf base: Acute.

Flowering description: Flowers open one at a time on the individual flower stalks.

A. *Fully expanded.*—35 to 40 mm.

B. *Stem.*—Single, green with reddish cast, long, slightly pubescent and round — several from a leaf midrib.

C. *Form.*—Funnel shaped in an umbel with upper two petals reflexed and lower petals flattened. Results in flat appearing flower.

D. *Flower bud description.*—20 to 25 mm at maturity, tubular with the end larger in diameter than the rest of bud. 5 green calyx folded over basal end.

E. *Flowers borne.*—In clusters of 2 to 4 flowers per flower stalk, with 4 the most common; carried above the foliage. Pedicels of the flowers in the inflorescence vary in length.

F. *Quantity of flowers.*—Mature plant can have more than 25 flower stalks open with up to 4 flowers per stalk.

G. *Permanence.*—Long lasting, 10 days or longer.

Color:

A. *Tonality from a distance.*—Light lavender pink with deeper carmine streaking extending out into the lower 3 petals. Two light yellow streaks visible from the throat.

B. *Upper surface of petals.*—74D, with 74B streaking on lower petals, and 150C streaking from eye.

C. *Under side of petals.*—76C.

D. *Throat.*—74B with 150C streaking from lower part and 76C from top part of throat.

E. *Discoloration.*—Flowers turn to a lighter lavender pink before turning brown when flower is aged.

Petals:

A. *Texture.*—Satin.

B. *Appearance.*—Individually lobed with slight crenate margins; top 2 petals are reflexed and smaller than the bottom petals which are flat.

C. *Arrangement.*—Regularly united into an almost circular shape.

D. *Persistence.*—10 days or longer. Remain on plant in dry form until picked.

E. *Fragrance.*—None.

Reproductive organs:

A. *Stamens.*—2 fertile; 2 sterile; very small and not present in all flowers. Anther shape: 2 fertile interconnected and flat. Anther color: White. Filament: Attached to petals for 3 mm and free standing for 4 mm on the fertile ones. Pollen color: white.

B. *Pistils.*—Stigma shape: 2 lobed flattened, rounded at ends of lobes. Stigma color: white with slight gray cast. Stigma size: 2 mm across. Style color: white near stigma to light green near ovaries. Style size: 4 mm. Ovaries: numerous, 12–14 mm on receptive pistil, green.

Disease resistance: No disease problems to date.

Other important characteristics: Compact growth habit combined with a highly floriferous habit makes this cultivar suitable for 10 cm pot plant production. The long lasting, non-shattering flowers and pliable small leaves make shipping easy. Lack of major insect and disease and insect problems makes for a trouble-free crop.

I claim:

1. A new and distinct cultivar of Streptocarpus plant named Muse, as described and illustrated, and particularly characterized by its rosette plant form, red-purple flower color with darker streaking, compact growth habit, floriferous habit, ease of propagation, tolerance to light and temperature, small, pliable leaves, and by its long lasting and non-shattering flowers.

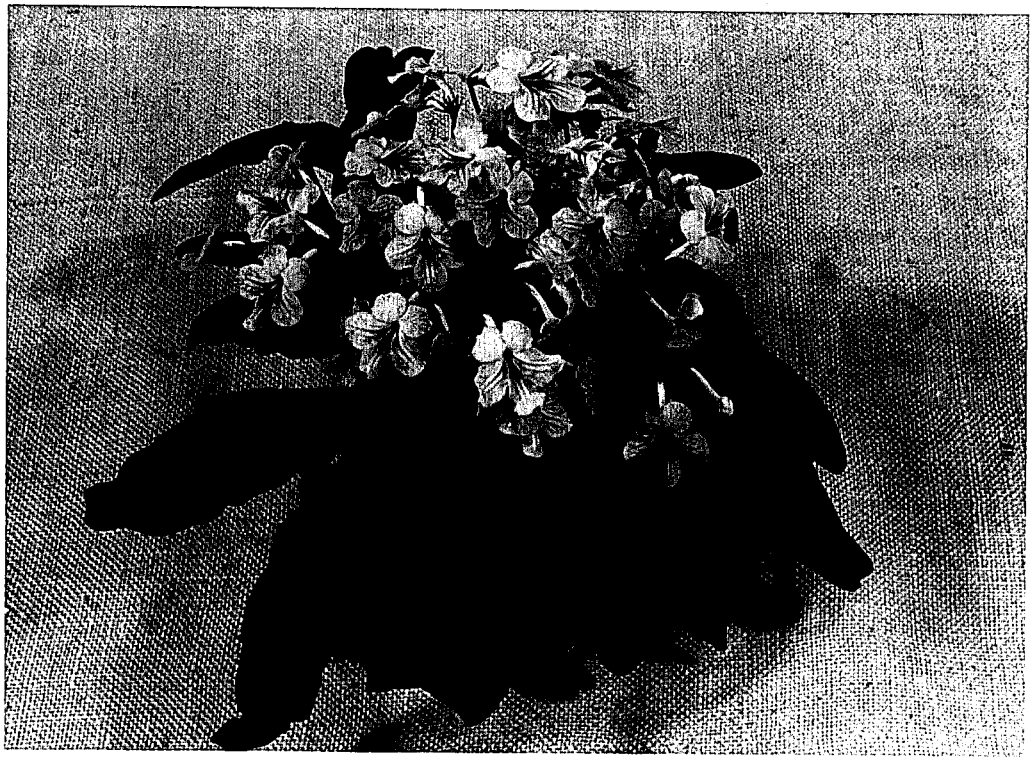

* * * * *